(12) United States Patent
Salminen

(10) Patent No.: US 10,357,667 B2
(45) Date of Patent: Jul. 23, 2019

(54) HIGH INTENSITY FOCUSED ULTRASOUND POSITIONING MECHANISM

(75) Inventor: Heikki Salminen, Klaukkala (FI)

(73) Assignee: Profound Medical Inc., Mississauga, ON (CA)

(*) Notice: Subject to any disclaimer, the term of this patent is extended or adjusted under 35 U.S.C. 154(b) by 575 days.

(21) Appl. No.: 13/496,043

(22) PCT Filed: Sep. 15, 2010

(86) PCT No.: PCT/IB2010/054161
§ 371 (c)(1),
(2), (4) Date: Mar. 14, 2012

(87) PCT Pub. No.: WO2011/036607
PCT Pub. Date: Mar. 31, 2011

(65) Prior Publication Data
US 2012/0172706 A1    Jul. 5, 2012

(30) Foreign Application Priority Data

Sep. 24, 2009  (EP) .................................. 09171200

(51) Int. Cl.
*A61B 5/05*  (2006.01)
*A61N 7/02*  (2006.01)
(Continued)

(52) U.S. Cl.
CPC .......... *A61N 7/02* (2013.01); *A61B 2090/374* (2016.02); *A61N 2007/0091* (2013.01)

(58) Field of Classification Search
CPC ...... A61B 2019/5236; A61B 2090/378; A61B 8/12; A61B 8/445; A61B 2018/00642;
(Continued)

(56) References Cited

U.S. PATENT DOCUMENTS 6,027,457 A * 2/2000 Shmulewitz et al. ......... 600/562
6,208,142 B1 * 3/2001 Wagshul ....................... 324/319
(Continued)

FOREIGN PATENT DOCUMENTS

CN     1550775 A      12/2004
CN     200963445 Y    10/2007
(Continued)

*Primary Examiner* — Baisakhi Roy
(74) *Attorney, Agent, or Firm* — Intrinsic Law Corp.

(57) ABSTRACT

A high intensity focused ultrasound positioning mechanism (100, 200, 310) for positioning a high intensity focused ultrasound transducer (292, 304), the mechanism comprising: —a positioning plate (108, 308) adapted for receiving the high intensity focused ultrasound transducer; —a mechanism support (174) adapted for mounting the positioning mechanism; —a plurality of rods (110, 112, 114, 116, 118, 120, 210, 212, 214, 216, 218, 220), wherein each rod has a first end and an second end, wherein the first end of each rod forms a separate ball joint (122, 124, 126, 128, 130, 132, 222, 224, 226, 228, 230, 232) with the positioning plate; and —a plurality of linear drives (146, 148, 150, 246, 248, 250, 252, 254), wherein the plurality of linear drives are mounted to the mechanism support, wherein each of the linear drives comprises a drive block (164, 166, 168, 264, 266, 268, 270, 272), wherein the second end of each of the plurality of rods forms a separate ball joint (134, 136, 138, 140, 142, 144, 234, 236, 238, 240, 242, 244) with one of the drive blocks.

12 Claims, 12 Drawing Sheets

(51) Int. Cl.
*A61N 7/00* (2006.01)
*A61B 90/00* (2016.01)

(58) Field of Classification Search
CPC ... A61B 8/4281; A61N 2007/009; A61N 7/02
USPC .......................... 600/437, 439, 410; 607/96
See application file for complete search history.

(56) References Cited

U.S. PATENT DOCUMENTS

| | | |
|---|---|---|
| 2003/0005786 A1 | 1/2003 | Stuart et al. |
| 2005/0154295 A1 | 7/2005 | Quistgaard et al. |
| 2005/0154431 A1* | 7/2005 | Quistgaard et al. ............ 607/96 |
| 2005/0250070 A1* | 11/2005 | Hamman ........................ 433/88 |
| 2007/0078343 A1* | 4/2007 | Kawashima et al. ......... 600/443 |
| 2008/0147056 A1* | 6/2008 | van der Weide et al. ...... 606/33 |
| 2008/0219652 A1* | 9/2008 | Pitkin et al. ...................... 396/4 |
| 2009/0054772 A1* | 2/2009 | Lin et al. ...................... 600/439 |
| 2009/0062869 A1* | 3/2009 | Claverie et al. .............. 606/324 |
| 2009/0069667 A1 | 3/2009 | Lindstrom |
| 2010/0246332 A1* | 9/2010 | Huang ........................... 367/181 |
| 2012/0035473 A1* | 2/2012 | Sanghvi et al. ............... 600/439 |
| 2013/0165974 A1* | 6/2013 | Kim ............................... 606/249 |

FOREIGN PATENT DOCUMENTS

| | | |
|---|---|---|
| DE | 19963194 A1 | 7/2001 |
| EP | 1348385 A1 | 10/2003 |
| WO | 2005107870 A1 | 11/2005 |
| WO | 2008026134 A1 | 3/2008 |

\* cited by examiner

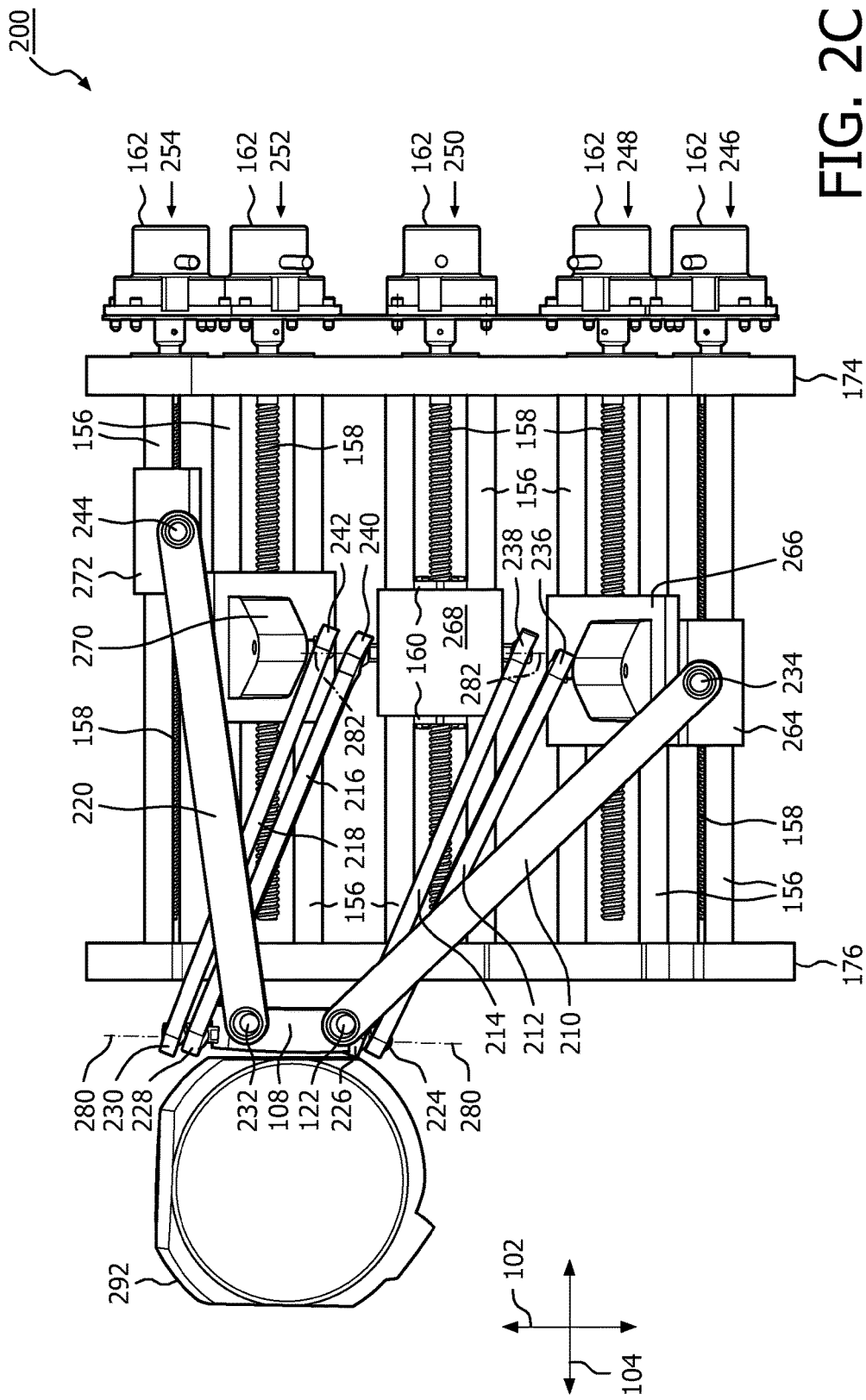

HIGH INTENSITY FOCUSED ULTRASOUND POSITIONING MECHANISM

TECHNICAL FIELD

The invention relates to a positioning mechanism, in particular a positioning mechanism for positioning a high intensity focused ultrasound transducer in a high intensity focused ultrasound system.

BACKGROUND OF THE INVENTION

In high intensity focused ultrasound, focused ultrasound is used for sonicating or treating a region of tissue within a subject with high intensity focused ultrasound. The high intensity focused ultrasound can be used for heating a region within the subject, it can be used for rupturing tiny capsules of a drug and activating the drug, it can be used for ablating tissue, and at higher powers cavitation can be used to destroy regions within the subject. High intensity focused ultrasound is focused onto a region of the subject using a transducer. Very often the transducers have multiple elements and by controlling the phase and amplitude of the individual elements the focus of the ultrasound within the subject can be adjusted to a certain degree. In addition to controlling the phase and amplitude of ultrasound emitted by elements of the ultrasound transducer, very typically the transducer is physically moved. For treatment of the breast, typically three degrees of freedom are used for mechanically moving the high intensity focused ultrasound transducer. In other modes of treatment therapy, such as for treating fibroids, five degrees of freedom are used.

When a region of a subject is sonicated, detailed information about the anatomy or internal structure of the subject is beneficial. As a result sonication of the subject is typically guided using a medical imaging modality. An example of such a medical imaging modality is magnetic resonance imaging.

International Patent application publication WO 2008/026134 A1 discloses a manipulator for controlling the position of an energy radiator.

SUMMARY OF THE INVENTION

The invention provides for a high intensity focused ultrasound positioning mechanism, a high intensity focused ultrasound unit, a magnetic resonance imaging system, a method of actuating a high intensity focused ultrasound positioning mechanism, and a computer program product in the independent claims. Embodiments are given in the dependent claims.

When using magnetic resonance imaging for guiding high intensity focused ultrasound, there are special requirements that are placed on the mechanism which is used for actuating or moving the high intensity focused ultrasound transducer. For instance all the parts may be non magnetic materials and may be able to tolerate the ultrasound conducting medium which the high intensity focused ultrasound transducer is immersed in, the construction of the mechanism is placed into a watertight container so the mechanism may also be watertight, the space available for the mechanism is extremely limited, because the bore or the region of the magnet for magnetic resonance imaging needs to accommodate both the patient, the mechanism and the high intensity focused ultrasound unit. Using a larger mechanism requires the use of a magnet with a larger bore and therefore increases the cost of the combined magnetic resonance imaging and high intensity focused ultrasound unit. Conversely, if the mechanism is made smaller and more compact, then the required bore or region adapted for accommodating a subject within the magnetic resonance imaging magnet is reduced. In addition it is also beneficial if motors and sensors which are incorporated into the mechanism do not generate radio frequency noise.

The invention provides for a high intensity focused ultrasound positioning mechanism for positioning a high intensity focused ultrasound transducer. The mechanism comprises a positioning plate adapted for receiving the high intensity focused ultrasound transducer. The physical location or position of the positioning plate is adjusted or manipulated by actuating the positioning mechanism. As a high intensity focused ultrasound transducer may be mounted to the positioning plate, adjusting the position or location of the positioning plate adjusts the position or location or orientation of the high intensity focused ultrasound transducer. The mechanism further comprises a mechanism support adapted for mounting the positioning mechanism. The mechanism further comprises a plurality of rods. Each rod has a first end and a second end, wherein the first end of each rod forms a separate ball joint with the positioning plate.

A rod as used herein is understood to be a rigid body. A rod functions or is equivalent to a link in a linkage or mechanical linkage. The mechanism further comprises a plurality of linear drives. The plurality of linear drives is mounted to the mechanism support. Each of the linear drives comprises a drive block. The second end of each of the plurality of rods forms a separate ball joint with one of the drive blocks. A mechanism which embodies this has several advantages. A very compact mechanism can be constructed. The number of sliding parts can also be reduced. In addition an embodiment of such a mechanism allows the calculation of how the mechanism may be positioned to put the positioning plate in a particular position or place. This allows precise control and positioning of a high intensity focused ultrasound transducer.

A linear drive as used herein is an actuating mechanism or component which is adapted for moving in a linear or a straight direction. A linear drive may be constructed using a screw mechanism, a rod that is actuated, a hydraulic system, a linear motor, or a pneumatic system. A drive block as used herein is a block or a component to which a ball joint or a component of a ball joint may be mounted. A ball joint as used herein is a joint which provides a spherical degree of movement. A ball joint may use a ball and a socket or it may use a system of swiveling hinges. A ball joint may be constructed using a ball and a socket. A ball joint may be formed by placing either a socket or a ball at either of the first or second ends of one of the plurality of rods. If a ball is on a particular end of one of the plurality of rods, then a socket is mounted onto the piece with which the rod forms a ball joint. If a socket is located on the rod, then a ball which is adapted to be received by the socket is mounted on the plate or block to which the rod forms a ball joint. The positioning block may be a separate component or an ultrasonic transducer for a high intensity focused ultrasound system may function as a positioning block.

In another embodiment, the plurality of rods comprises a first rod, a second rod, a third rod, a fourth rod, a fifth rod and a sixth rod. The plurality of linear drives comprises a first linear drive, a second linear drive and a third linear drive. The first linear drive comprises a first drive block. The second linear drive comprises a second drive block. The third linear drive comprises a third drive block. The first end of the first rod forms a first ball joint with the positioning plate.

The first end of the second rod forms a second ball joint with the positioning plate. The first end of the third rod forms a third ball joint with the positioning plate. The first end of the fourth rod forms a fourth ball joint with the positioning plate. The first end of the fifth rod forms a fifth ball joint with the positioning plate. The first end of the sixth rod forms a sixth ball joint with the positioning plate.

The first rod forms a seventh ball joint with the first drive block. The second rod forms an eighth ball joint with the first drive block. The third rod forms a ninth ball joint with the second drive block. The fourth rod forms a tenth ball joint with the second drive block. The fifth rod forms an eleventh ball joint with the third drive block. The sixth rod forms an twelfth ball joint with the third drive block. This embodiment is advantageous, because a mechanism that embodies this will have three orthogonal degrees of freedom.

In another embodiment the first and second ball joints are mounted on a first common axis. The second and third ball joints are mounted on a second common axis. The fourth and fifth ball joints are mounted on a third common axis. The seventh and eighth ball joints are mounted on a fourth common axis. The ninth and tenth ball joints are mounted on a fifth common axis. The eleventh and twelfth ball joints are mounted on a sixth common axis. By stating that a ball joint is mounted on a common axis, it is understood that herein this means that the center of rotation for the ball joints which are mounted on a common axis are fixed on this axis.

In another embodiment the plurality of rods comprises a first rod, a second rod, a third rod, a fourth rod, a fifth rod and a sixth rod. The plurality of linear drives comprises a first linear drive, a second linear drive, a third linear drive, a fourth linear drive and a fifth linear drive. The first linear drive comprises a first drive block. The second linear drive comprises a second drive block. The third linear drive comprises a third drive block. The fourth linear drive comprises a fourth drive block. The fifth linear drive comprises a fifth drive block.

The first end of the first rod forms a first ball joint with the positioning plate. The first end of the second rod forms a second ball joint with the positioning plate. The first end of the third rod forms a third ball joint with the positioning plate. The first end of the fourth rod forms a fourth ball joint with the positioning plate. The first end of the fifth rod forms a fifth ball joint with the positioning plate. The first end of the sixth rod forms a sixth ball joint with the positioning plate.

The first rod forms a seventh ball joint with the first drive block. The second rod forms an eighth ball joint with the second drive block. The third rod forms a ninth ball joint with the third drive block. The fourth rod forms a tenth ball joint with the third drive block. The fifth rod forms an eleventh ball joint with the fourth drive block. The sixth rod forms a twelfth ball joint with the fifth drive block. This embodiment is advantageous, because the mechanism may be compact and has five degrees of freedom. This allows complex actuation of a high intensity focused ultrasound unit with a mechanism that uses a reduced amount of space.

In another embodiment the second, third, fourth and fifth ball joints are mounted on a first common axis. The ninth and tenth ball joints are mounted on a second common axis. This embodiment is advantageous, because placing these combinations of ball joints on these common axes provides for a mechanism where its position can be calculated more simply.

In another embodiment at least one of the plurality of linear drives comprises a linear slide, a screw drive, and a bearing. At least one of the plurality of linear drives is actuated by an ultrasound motor. A screw drive as used herein is a drive which translates rotational into translational motion. A screw drive can function with threads or it may also be a ball screw drive or a sliding screw drive. A sliding screw drive uses elements which slide over the threads of a drive rod. A linear side as used herein is a block which is driven in a linear or straight fashion. A linear slide may also function as a drive block. The terms linear slide and drive block may be used as synonyms herein. If a linear slide and a drive block are separate components, a drive block may be attached to the linear slide. The linear slide may be prevented from rotating by a surface or a rod. The friction between the linear slide and the guiding surface or rod may be reduced by the bearing. The at least one of the plurality of linear drives is actuated by an ultrasound motor.

In another embodiment at least one of the plurality of linear drives is actuated using a hand crank.

In another embodiment the linear slide, the screw drive and the bearing are ceramic. This embodiment is advantageous, because high intensity focused ultrasound units are typically immersed in a liquid for the purpose of conducting ultrasound. A ceramic linear slide, screw drive and bearing would be able to survive in a fluid or liquid environment for an extended period of time.

In another embodiment at least one of the plurality of rods comprises plastic. The use of plastic for the rods is advantageous in several situations. In a magnetic resonance imaging system this is advantageous because the amount of metal which is used is reduced. In addition the rod can be constructed of a single piece with the sockets for the ball joint molded in the ends. This eliminates the need for fixing sockets for the ball joints on the rods.

In another embodiment, at least one of the plurality of rods comprises acetal polyoxynethylene plastic.

In another embodiment at least one of the first through twelve balls comprises a titanium ball. The use of titanium balls is advantageous, because titanium is compatible with large magnetic fields and can thus be used in a magnetic resonance imaging system. In general titanium is a very hard metal and is very suitable for use as a bearing. Titanium is also very chemically resistant and is therefore a good choice for a bearing in a system which is submersed in a liquid for an extended period of time.

In another aspect, the invention provides for a high intensity focused ultrasound unit. The high intensity focused ultrasound unit comprises a mechanism according to an embodiment of the invention. The high intensity focused ultrasound unit further comprises an actuation system for actuating the mechanism. The high intensity focused ultrasound unit further comprises a control system for controlling the actuation system. The high intensity focused ultrasound unit further comprises a high intensity focused ultrasound transducer. The high intensity focused ultrasound unit further comprises a patient support adapted for receiving a subject.

An actuation system is any system which is adapted for actuating the mechanism. In the case of a screw drive, the actuation system would provide for rotational motion. An ultrasonic or stepping motor would be an example of an embodiment of an actuation system. The mechanism functions using linear motion, so a piston which uses air or pneumatic fluid could also be used for actuating the mechanism. A control system for controlling the actuation system could have several different embodiments. A control system could simply be a system which receives instructions from another controller or computer system and then the control system simply executes these commands and controls the actuation system to properly actuate the mechanism.

The control system could also be more sophisticated, it could include a processor which is capable of performing the calculations necessary to actuate the mechanism along a predetermined path between a first point and a second point. In this case the control system may be a processor which is capable of modeling the motion of the mechanism. An embodiment of this invention of this high intensity focused ultrasound unit is advantageous, because the mechanism may use a reduced amount of space. This provides for a more compact high intensity focused ultrasound unit.

In another aspect, the invention provides for a magnetic resonance imaging system. The magnetic resonance imaging system comprises a high intensity focused ultrasound unit according to an embodiment of the invention. The magnetic resonance imaging system further comprises a magnet for generating a magnetic field for orientating the magnetic spins of nuclei. The magnetic resonance imaging system further comprises a radio frequency system comprising a coil calibrated for acquiring magnetic resonance imaging data. Magnetic resonance imaging data is defined herein as data which is received by the coil and was emitted by the magnetic spins of nuclei. Magnetic resonance imaging data may be reconstructed into magnetic resonance imaging images.

The magnetic resonance imaging system further comprises a magnet field gradient coil for spatial encoding of the orientation of magnetic spins of nuclei. The magnetic resonance imaging system further comprises a magnetic field gradient coil power supply for supplying current to the magnetic field gradient coil. The magnetic resonance imaging system further comprises a computer system for constructing images from the magnetic resonance imaging data and for controlling the operation of the magnetic resonance imaging system. The computer system is adapted for controlling the high intensity focused ultrasound unit. The computer system may actually control the operation of the high intensity focused ultrasound unit, or alternatively it may send commands to the high intensity focused ultrasound unit and a computer system or onboard processing system in the high intensity focused ultrasound unit uses these commands to generate commands which control the production of ultrasound by the ultrasound transducer and also control the actuation of the mechanism.

A computer system as used herein is defined as a machine adapted for performing machine executable instructions. A computer system may be a single computer, a group of computers, a network of computers, an embedded system, a microcontroller or other system adapted for executing machine executable computer programs.

In another aspect the invention provides for a method of actuating a high intensity focused ultrasound positioning mechanism according to an embodiment of the invention. The method comprises the step of calculating a trajectory of the mechanism from a first position to a second position. The trajectory of the mechanism is a path that the mechanism follows. The trajectory may simply be a path, or it may also be a time dependent path. Part of a treatment plan could be a trajectory that the high intensity focused ultrasound unit follows. The method further comprises generating an actuation plan using the calculated trajectory. The actuation plan is a representation of the actuation of the mechanism which is necessary for following the trajectory. The actuation plan could be a machine readable actuation plan and contain instructions for a controller to send to the actuators to move the mechanism along the trajectory. The actuation plan could also be a set of coordinates that could be used to move the mechanism along the trajectory. In the case of manual actuation these could be a set of dial settings or coordinates that an operator dials on the mechanism. Calculating a trajectory of the mechanism from a first position to a second position it is understood that the trajectory is a predetermined position on the positioning plate. The first position and the second position can also be defined in terms of the geometry of the high intensity focused ultrasound transducer which may be attached to the positioning plate. The method further comprises actuating the mechanism from the first position to the second position using the actuation plan. In an automated system the actuator plan is used by a controller or computer system to control an actuation system. In the case of a manual operator an operator manually actuates the mechanism using a manual system or by using control levers or switches or buttons.

In another aspect the invention provides for a computer program product comprising machine executable instructions for execution by a control system. The control system is adapted for controlling the actuation of a high intensity focused ultrasound positioning mechanism according to an embodiment of the invention. The computer program product comprises the step of calculating a trajectory of the mechanism from a first position to a second position, generating an actuation plan using the calculated trajectory and actuating the mechanism from the first position to the second position using the actuation plan.

BRIEF DESCRIPTION OF THE DRAWINGS

In the following preferred embodiments of the invention will be described, by way of example only, and with reference to the drawings in which:

FIG. 2c illustrates the same embodiment of a mechanism as shown in FIG. 2a from another view;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
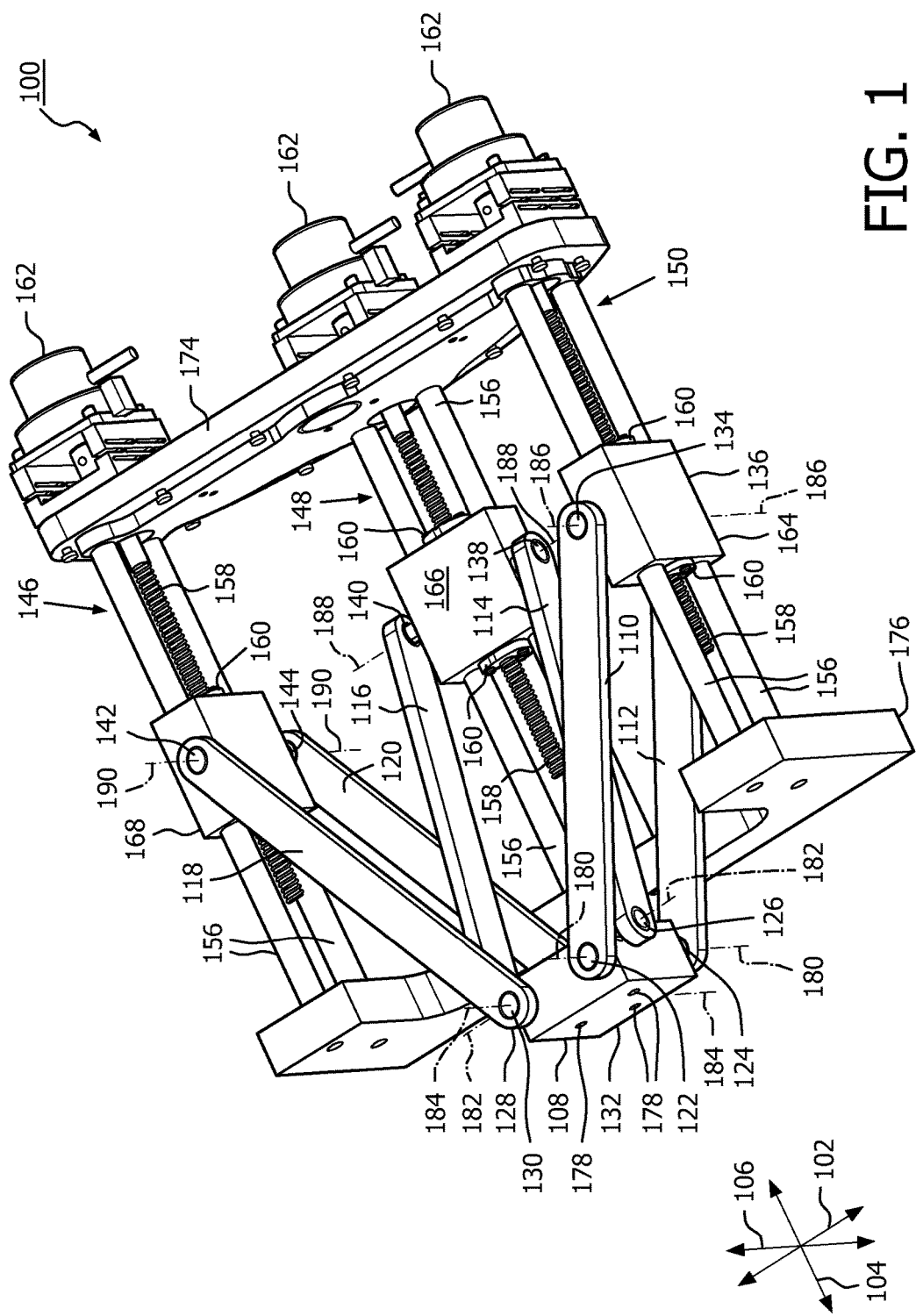
FIG. 1 illustrates a mechanism according to an embodiment of the invention.

FIG. 1 shows a mechanism 100 according to an embodiment of the invention. This mechanism has three linear drives 146, 148, 150. The mechanism 100 is adapted for moving the positioning plate 108 along three orthogonal axes, the x axis 102, the y axis 104, and the z axis 106. The choice of x, y and z for labeling the axes is an arbitrary choice. In FIG. 1 a first rod 110, a second rod 112, a third rod 114, a fourth rod 116, a fifth rod 118, and a sixth rod 120 are shown. The first rod 110 forms a first ball joint 122 with the positioning plate 108. The second rod 112 forms a second ball joint 124 with the positioning plate 108. The third rod 114 forms a third ball joint 126 with the positioning plate 108. The fourth rod 116 forms a fourth ball joint 128 with the positioning plate 108. The fifth rod 118 forms a fifth ball joint 130 with the positioning plate 108. The sixth rod 120 forms a sixth ball joint 132 with the positioning plate 108. The first rod 110 forms a seventh ball joint 134 with the first drive block 164. The second rod 112 forms an eighth ball joint 136 with the first drive block 164. The third rod 114 forms a ninth ball joint 138 with the second drive block 166. The fourth rod 116 forms a tenth ball joint 140 with the second drive block 166. The fifth rod 118 forms an eleventh ball joint 142 with the third drive block 168. The sixth rod 120 forms a twelfth ball joint 144 with the third drive block 168.

Shown in FIG. 1 is a first linear drive 146, a second linear drive 148 and a third linear drive 150. Each linear drive comprises rods 156. The rods are used for guiding the drive blocks. The first linear drive 146 comprises the first drive block 164. The second linear drive 148 comprises the second drive block 166. The third linear drive 150 comprises the third drive block 168. The rods 156 prevent the drive blocks from turning or twisting as they are driven by the screw drive rod 158. Also mounted within each of the drive blocks 164, 166, 168 are threaded elements 160. The threaded elements 160 in this embodiment contains threads. In another embodiment a ball screw drive could be used. The screw drive rods 158 are driven by ultrasonic motors 162. The use of ultrasonic motors allows the very precise control of the mechanism. The linear drives 146, 148, 150 are mounted onto the mechanism support 174. In this case the mechanism support is a plate. This plate can be bolted into a high intensity focused ultrasound unit and may form a watertight seal as it is bolted into place. The rods 156 are mounted onto the mechanism support. Opposing the mechanism support is a plate 176 which the rods 156 are also attached to. The combination of the plate 176, the mechanism support 174 and the rods 156 forms a rigid structure for the mechanism. Visible on the positioning plate 108 are threaded holes 178 for mounting an ultrasonic transducer. The first ball joint 122 and the second ball joint 124 are mounted along a first common axis 180. The second 124 and third 126 ball joints are mounted along a second common axis 182. The third ball joint 126 and fourth ball joint 128 are mounted along a third common axis 184. The first 180, second 182 and third 184 axes pass through the positioning plate 108. The seventh ball joint 134 and eighth ball joint 136 form a fourth common axis 186. The fourth common axis passes through the first drive block 164. The ninth ball joint 138 and the tenth ball joint 140 are mounted on a fifth common axis 188. The fifth common axis 188 passes through the second drive block 166. The eleventh ball joint 142 and the twelfth ball joint 144 are mounted along a sixth common axis 190. The sixth common axis 190 passes through the third drive block 168.

In this embodiment the first 146, second 148, and third 150 linear drives are mounted on the mechanism support 174 such that they provide linear motion that is parallel to the y axis. It is not required that all three linear drives are aligned nor is it required that they are along the so called y axis 104. However, it is beneficial because then the positioning plate 108 moves orthogonally to the x 102, y 104, and z 106 axes. In this embodiment the first common axis 180, the third common axis 184, the fourth common axis 186 and the sixth common axis 190 are all parallel with the z axis 106. The second common axis 182 and the fifth common axis 188 are parallel with the x axis 102. Again, it is not necessary that these axes are aligned such, however, the alignment of the axes in this fashion in combination with the alignment of the linear drives 146, 148, 150 with the y axis 104 allows for a simplified calculation of the position of the positioning plate 108 and also ensures that the motion of the positioning plate 108 is orthogonal with the x axis 102, y axis 104 and z axis 106.

In operation the first linear drive 146, second linear drive 148 and third linear drive 150 would typically all be operated at the same time. The reason for this is that when any one ultrasonic motor 162 is activated the positioning block 108 will move in more than one of the orthogonal directions indicated by the x axis 102, y axis 104 or z axis 106. It is therefore beneficial to move all three simultaneously such that the mechanism moves following a predefined path or moving following just one of the axes 102, 104, 106.

Figure 2A:
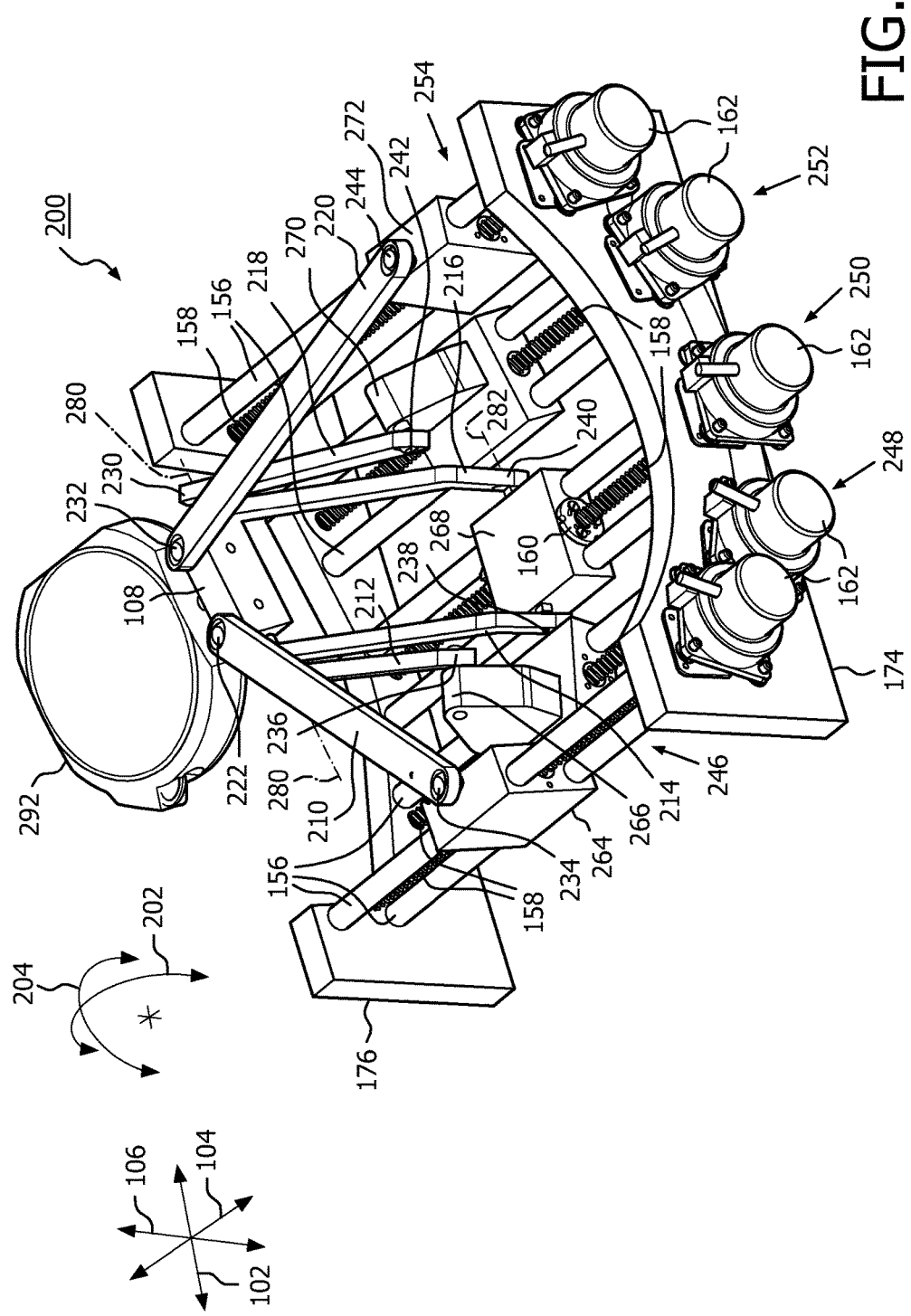
FIG. 2a illustrates a mechanism according to a further embodiment of the invention.
Figure 2B:
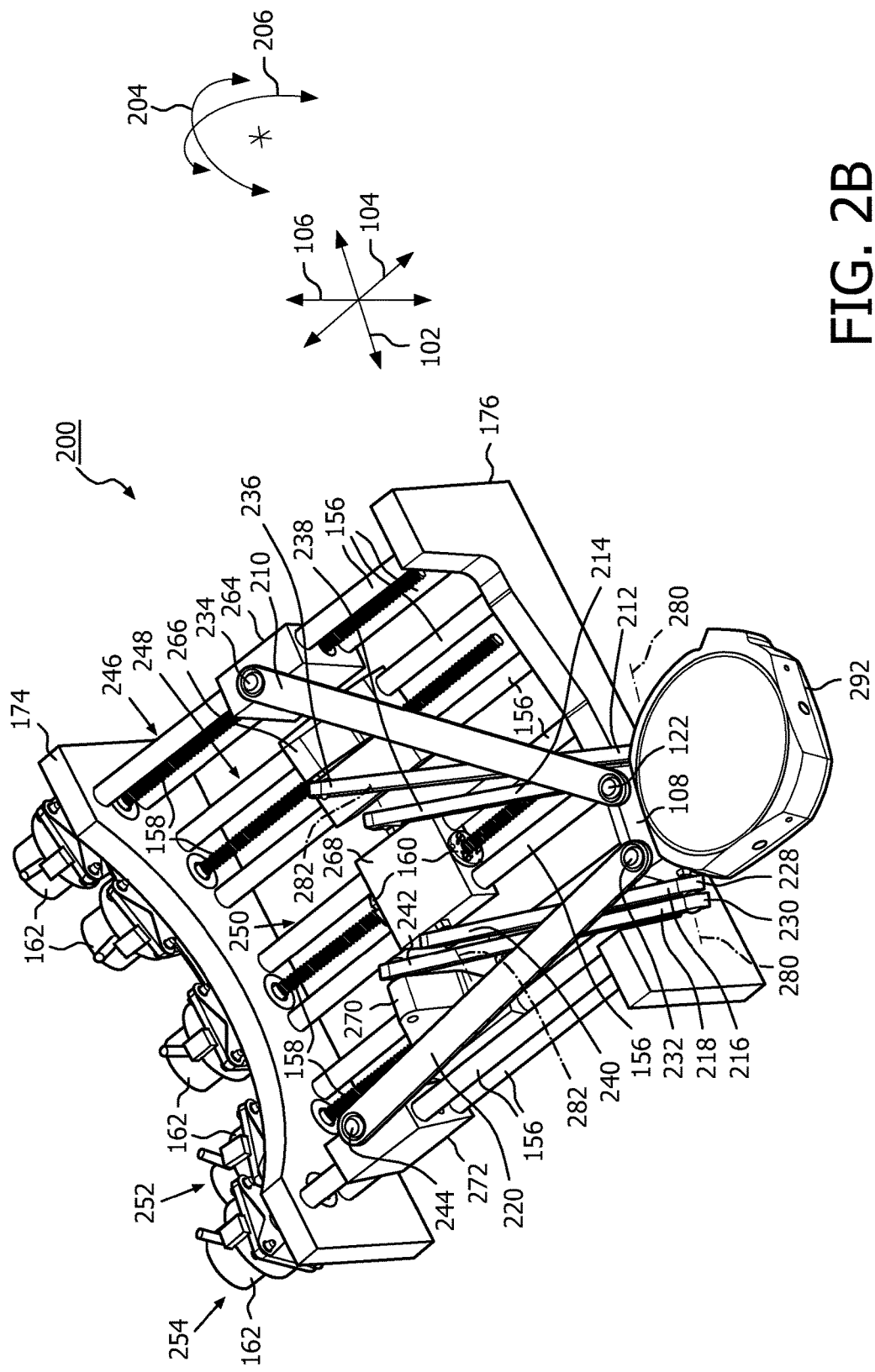
FIG. 2b illustrates the same embodiment of a mechanism as shown in FIG. 2a from another view.
Figure 2D:
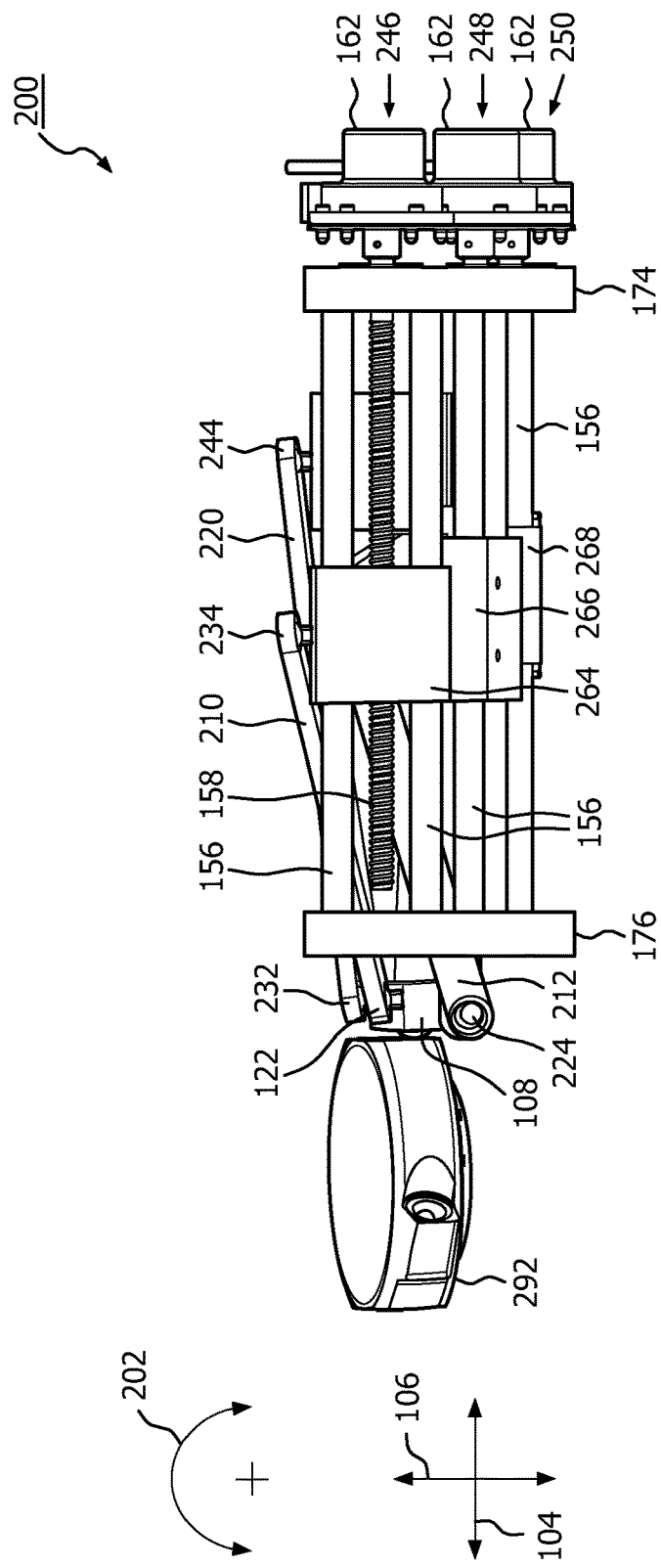
FIG. 2d illustrates the same embodiment of a mechanism as shown in FIG. 2a from another view.

FIGS. 2a, 2b, 2c and 2d show the same embodiment of a mechanism 200 according to the invention from different views. FIGS. 2a and 2b show perspective views. FIG. 2c shows a top view and FIG. 2d shows a side view. In this embodiment there are five linear drives 246, 248, 250, 252, 254. This mechanism 200 has five degrees of freedom. These are illustrated in the Fig. with the x axis 102, the y axis 104, and the z axis 106. This mechanism also allows rotation of the positioning plate 108 about the x axis 202 and about the z axis 204. Shown in these figures is a first rod 210, a second rod 212, a third rod 214, a fourth rod 216, a fifth rod 218, and a sixth rod 220. The first rod 210 and the positioning plate 208 form a first ball joint 222. The second rod 212 and the positioning plate 208 form a second ball joint 224. The third rod 214 and the positioning plate 208 form a third ball joint 226. The fourth rod 216 and the positioning plate 208 form a fourth ball joint 228. The fifth rod 218 and the positioning plate 208 form a fifth ball joint 230. The sixth rod 220 and the positioning plate 208 form a sixth ball joint 232. There is a first linear drive 246, a second linear drive 248, a third linear drive 250, a fourth linear drive 252, and a fifth linear drive 254. The first linear drive 246 has a first drive block 264. The second linear drive 248 has a second drive block 266. The third linear drive 250 has a third drive block 268. The fourth linear drive 252 has a fourth drive block 270. The fifth linear drive 254 has a fifth drive block 272. The first rod 210 and the first drive block 264 form a seventh ball joint. The second rod 212 and the second drive block 266 form an eighth ball joint 236. The third rod 214 and the third drive block 268 form a ninth ball joint 238. The fourth rod 216 and the third drive block 268 form a tenth ball joint 240. The fifth rod 218 and the fourth drive block 270 form an eleventh ball joint 242. The sixth rod 220 and the fifth drive block 272 form a twelfth ball joint 244.

Each of the linear drives 246, 248, 250, 252, 254 have rods 156 which guide the drive blocks 264, 266, 268, 270, 272 and ensure that they move in a linear fashion. Each of the linear drives 246, 248, 250, 252, 254 also have screw drives rods 158, threaded elements 160, and ultrasonic motors 162 as were described in the embodiment in FIG. 1 also. Threaded elements 160 are only shown on the third drive block 268 in this figure. In practice threaded elements would also be mounted on the first drive block 264, second drive block, 266, fourth drive block 270, and fifth drive block 272. The linear drives 246, 248, 250, 252, 254 are secured to a mechanism support 174. The mechanism support 174 and the rods 156 form a stable framework for the mechanism 200. As with the embodiment in FIG. 1 the linear drives 246, 248, 250, 252, 254 are all aligned with the y axis 104 such that the drive blocks 264, 266, 268, 270, 272 all move parallel with the y axis 104.

The first ball joint 222, the second ball joint 224, the fifth ball joint 230, and the sixth ball joint 232 are all mounted such that they are aligned with a first common axis 280. The first common axis 280 passes through the positioning plate 108. The ninth ball joint 238 and the tenth ball joint 240 are both aligned and mounted on a second common axis 282. The second common axis is with the x axis 102. The linear drives and the second common axis 282 do not need to be aligned in this fashion, but it is advantageous because it allows for a mechanism which it is easier to calculate the actuation of the linear drives such that the positioning plate 108 is moved into a desired position. In this figure an ultrasonic transducer 292 is shown mounted to the positioning plate 108.

As with the embodiment shown in FIG. 1, it may be advantageous to move a combination of ultrasonic motors 162 simultaneously during actuation of the mechanism 200. This is because when any one ultrasonic motor 162 is moved, the positioning plate 108 will not move in a single orthogonal direction 102, 104, 106, 202, 204.

Figure 3:
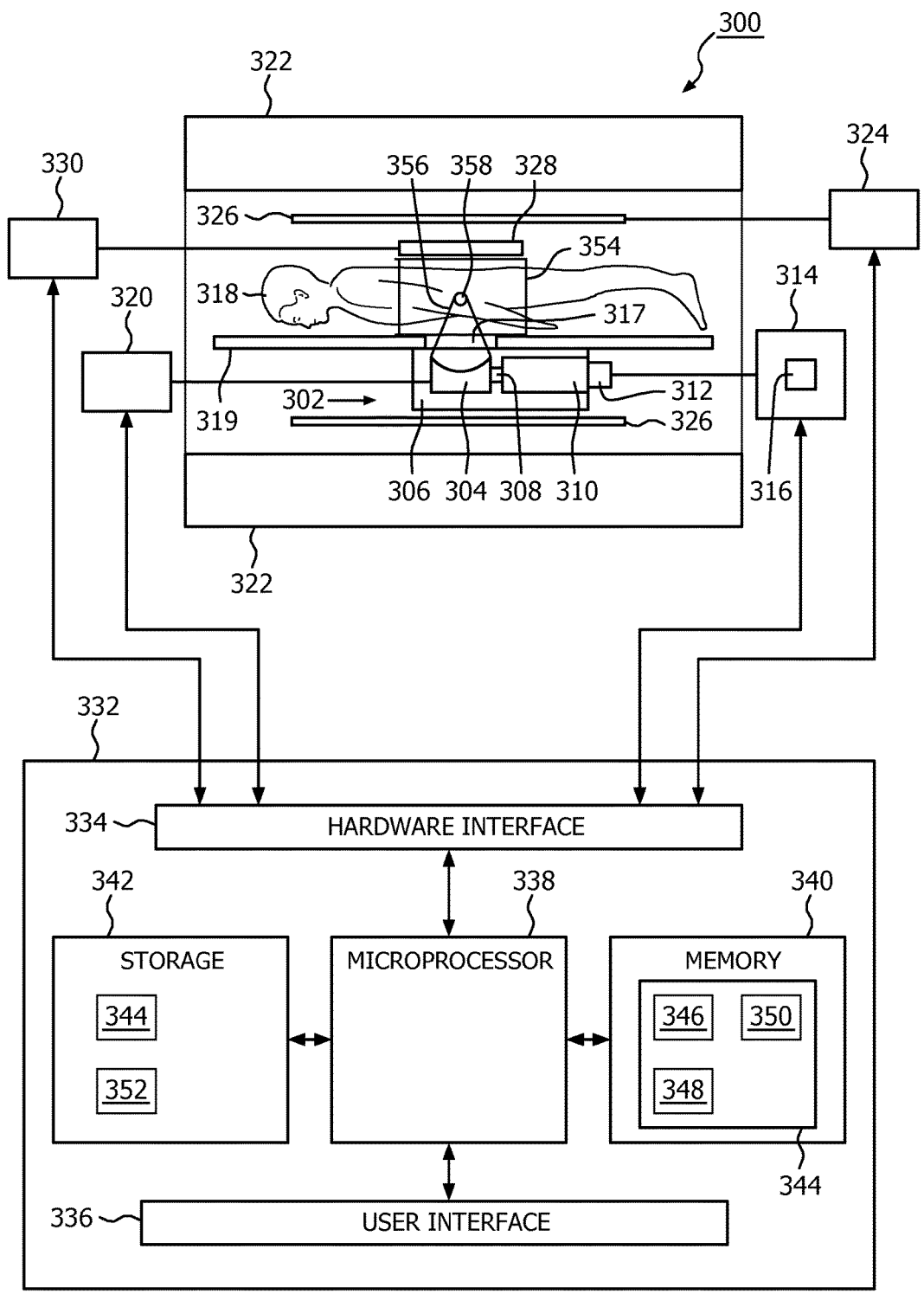
FIG. 3 shows a functional diagram of a combined magnetic resonance imaging system and high intensity focused ultrasound system according to an embodiment of the invention.

FIG. 3 shows a magnetic resonance imaging system according to an embodiment of the invention. The magnetic resonance imaging system 300 comprises a high intensity focused ultrasound system 302 according to an embodiment of the invention. In the high intensity focused ultrasound system 302 is a transducer 304 that is located within a fluid filled region 306. The ultrasound transducer 304 is attached to a positioning block 308 of a mechanism 310 according to an embodiment of the invention. The mechanism 310 is actuated by an actuation system 312. The actuation system 312 is connected to a control system 314 which is adapted for controlling the actuation system 312. A component of the control system is an embedded system 316. The embedded system is adapted for calculating the proper actuation of the mechanism 310 in order to move the transducer 304 from a first position to a second position. A subject 318 is shown on a subject support 319. There is a gap in the subject support 317 which allows the ultrasound to follow path 356 into the subject 318. The gap 317 may be adapted for receiving an ultrasound coupling medium such as a gel pad or ultrasonic coupling gel to ensure proper ultrasonic coupling between the high intensity focused ultrasound system 302 and the subject 318. The ultrasound is focused at a sonication zone 358 within the subject 318. Not shown in the diagram is a ultrasound window which allows the ultrasound to pass from the high intensity focused ultrasound unit 302 through the gap in the subject support 317 and into the subject 318.

The magnetic resonance imaging system comprises a magnet 322. The magnet generates a magnetic field for orienting the magnetic spins and nuclei. The magnetic resonance imaging system 300 also comprises magnetic field gradient coil 326 which is used for generating magnetic field gradients which encode the spatial orientation of the spins in the nuclei. The magnetic field gradient coil is connected to a gradient power supply 324. The magnetic resonance imaging system 300 is adapted for acquiring magnetic resonance imaging data in an imaging zone 354. sonication zone 358 is within the imaging zone 354 and allows the magnetic resonance imaging system to guide the sonication of the subject 318. There is a radio frequency coil 328 which allows the acquisition of magnetic resonance imaging data within the imaging zone 354. The radio frequency coil 328 is connected to a radio frequency transceiver 330. The radio frequency coil 328 could be separate send and receive coils and the radio frequency transceiver 330 could also be separate transmitters and receivers. There is a computer system 332 which has a power system 334 which is adapted for controlling the combined magnetic resonance imaging 300 and high intensity focused ultrasound 302 systems. The hardware interface 334 is connected to the radio frequency transceiver 330, the transducer power supply is connected to the high intensity focused ultrasound transducer 304. Hardware interface 334 is also connected to the gradient power supply 324. The hardware interface 334 is also connected to the control system 314 that controls the high intensity focused ultrasound system 302.

In the computer system there is a microprocessor 338 which is adapted for executing machine executable instructions. The microprocessor is connected to a storage unit 342. The storage unit 342 is for storing computer readable data. Shown within the storage 342 is a computer program product 344 adapted for controlling the operation of the combined magnetic resonance imaging 300 and high intensity focused ultrasound 302 systems. The storage can also store other computer data such as imaging data 352. The microprocessor 338 is also connected to computer memory 340. In the computer memory is the computer program product 344. The computer program product 344 comprises a magnetic resonance imaging control module which allows the microprocessor to send commands to the hardware interface for controlling the operation of the magnetic resonance imaging system 300. There is also a high intensity focused ultrasound control module 348 which allows the microprocessor 338 to send control signals via the hardware interface 334 for controlling the high intensity focused ultrasound system 302. There is also an image reconstruction module which allows the microprocessor to reconstruct magnetic resonance imaging data into magnetic resonance imaging images. Finally, there is a user interface 336 which is connected to the microprocessor which allows the microprocessor to display images and provide an interface which allows an operator to control the operation of the computer system 332 and the combined magnetic resonance imaging system 300 and high intensity focused ultrasound 302 system.

Figure 4:
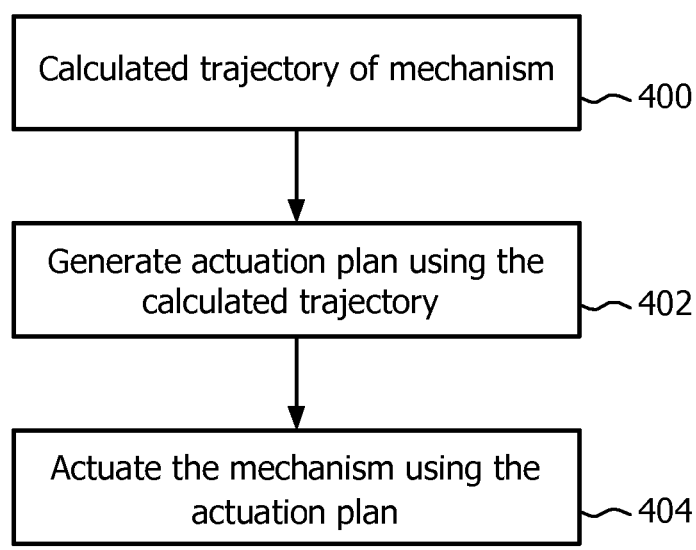
FIG. 4 is a block diagram illustrating a method according to an embodiment of the invention.

FIG. 4 shows an embodiment of a method according to the invention. In step 400 the trajectory of the mechanism is calculated. As was mentioned above, when a linear actuator is actuated the positioning plate will move in more than one of the degrees of freedom. In step 400 the trajectory is calculated. In step 402 the calculated trajectory is used to generate an actuation plan using the calculated trajectory. The calculated trajectory is used to either generate a set of instructions which an operator can use to properly actuate the mechanism or a set of machine readable instructions which can be used by a controller to actuate the mechanism. Finally, in step 404, the mechanism is actuated from the first position to the second position along the trajectory using the actuation plan.

Figure 5:
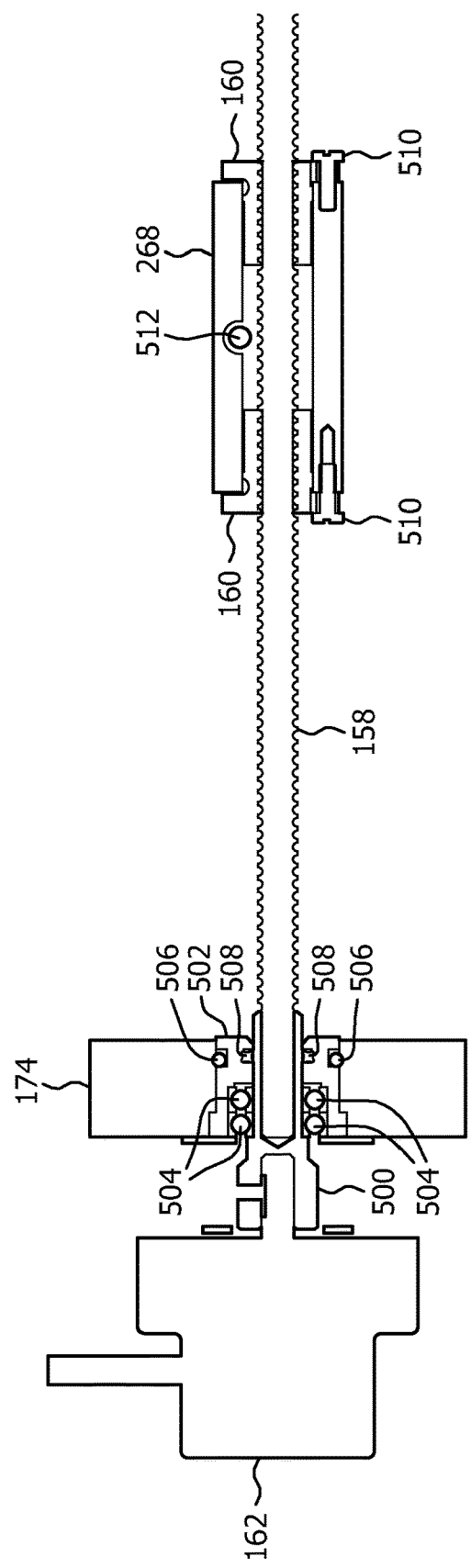
FIG. 5 shows a cross sectional view of a screw drive according to an embodiment of the invention.

FIG. 5 shows a cross sectional view of a screw drive according to an embodiment of the invention. The motor 162 is connected to a coupler 500. The coupler 500 is attached to the screw drive rod 158. The motor 162 and the coupler 500 are supported by an insert 502 which is connected to the mechanism support 174. Ball berings 504 are used to form a bearing between the insert 502 and the coupler 500. The coupler 502 and the mechanism support 174 are sealed using a static sealing element 502. The sealing element 502 in this embodiment is an O-ring, but in other embodiments the sealing element may have different forms. For example, the sealing element 502 could be a gasket. The insert 502 and the coupler 502 are sealed using a rotational sealing element. A rotational sealing element is a sealing element such as an O-ring which maintains a water tight or fluid tight seal when one of the elements that is being sealed is rotating. In this case the coupler 502 is adapted for rotating when actuating the mechanism.

The third drive block 268 of the embodiment shown in FIGS. 2a through 2d is shown. Threaded elements 160 are held in either end of the third drive block 268 using screws 510. In this embodiment, the threaded elements 160 are plastic and are pretensioned. Also visible is an axel 512. Titanium balls used to form the ninth and tenth ball joints are attached to this axel.

Figure 6:
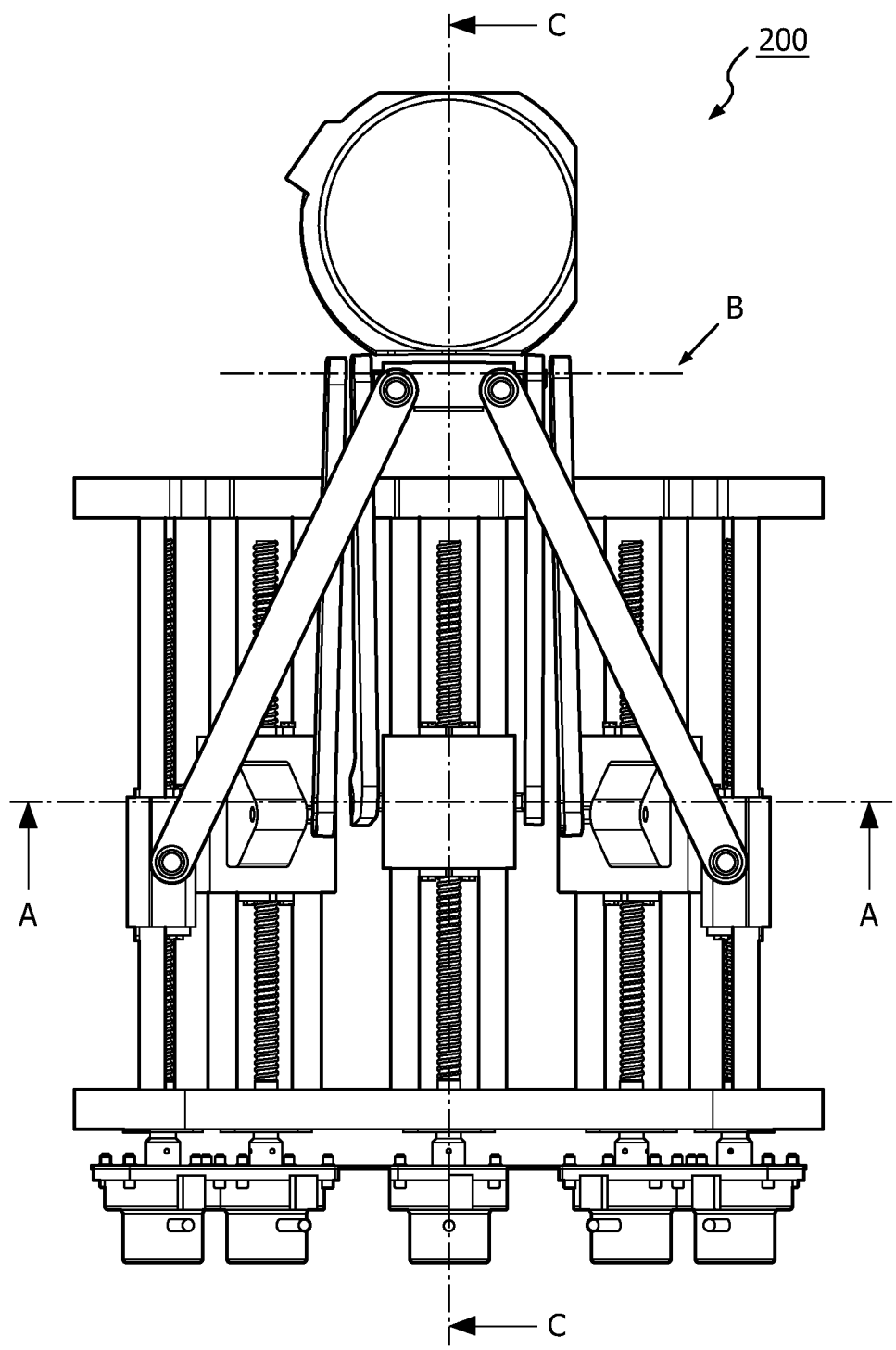
FIG. 6 shows a top view of the mechanism shown in FIGS. 2a through 2d with section lines A, B, and C labeled.

FIG. 6 shows a top view of the mechanism 200 shown in FIGS. 2a through 2d with section lines A, B, and C labeled.

Figure 7A:
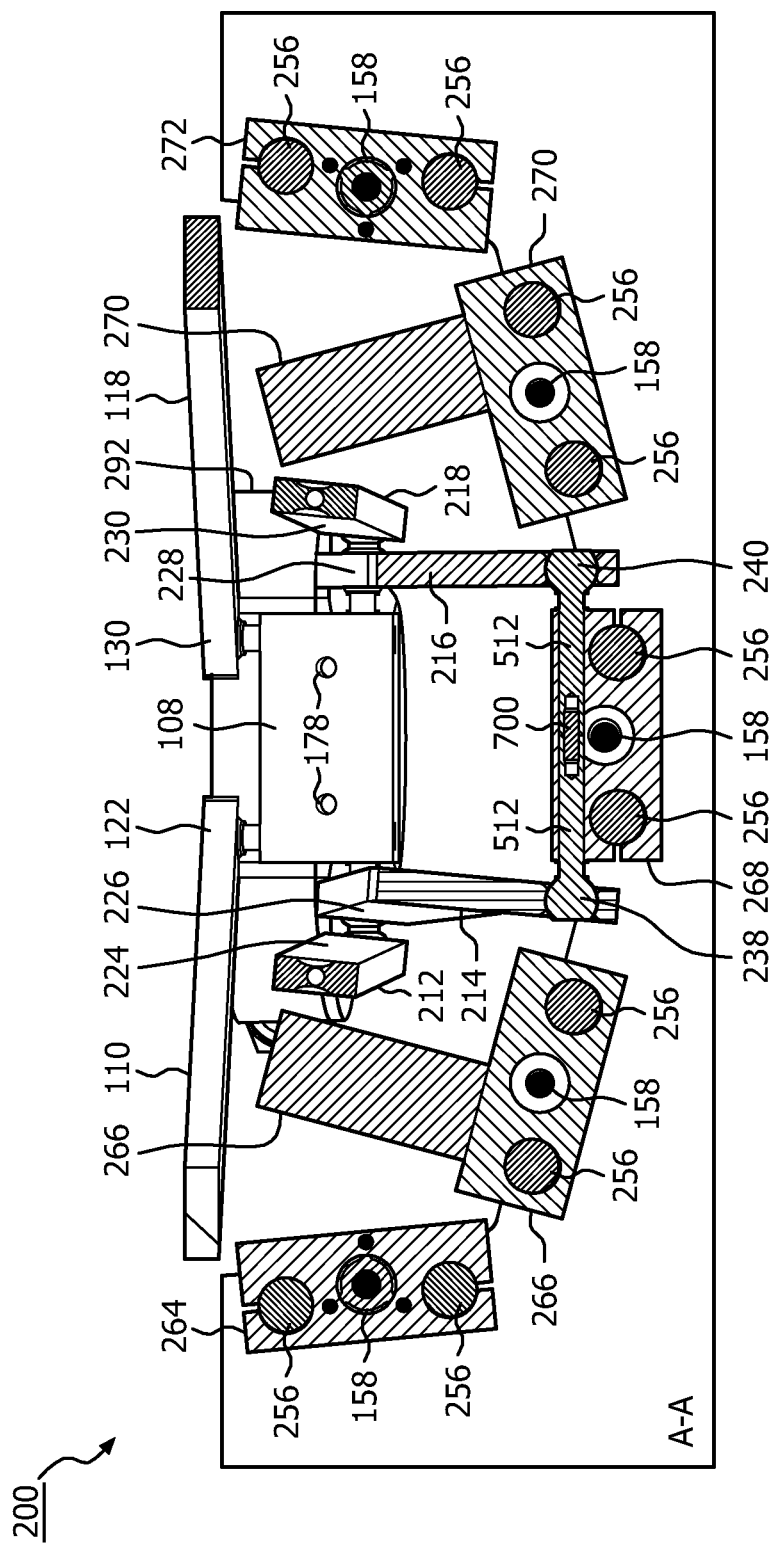
FIG. 7a shows a cross sectional view of the mechanism shown in FIGS. 2a through 2d along section line A.

FIG. 7A shows a cross sectional view of the mechanism 200 shown in FIGS. 2a through 2d along section line A. In this cross sectional view, the construction details of the ninth ball joint 238 and the tenth ball joint 240 are visible. Each of these ball joints 238, 240 are connected to an axel 512 which are connected using a threaded rod 700.

Figure 7B:
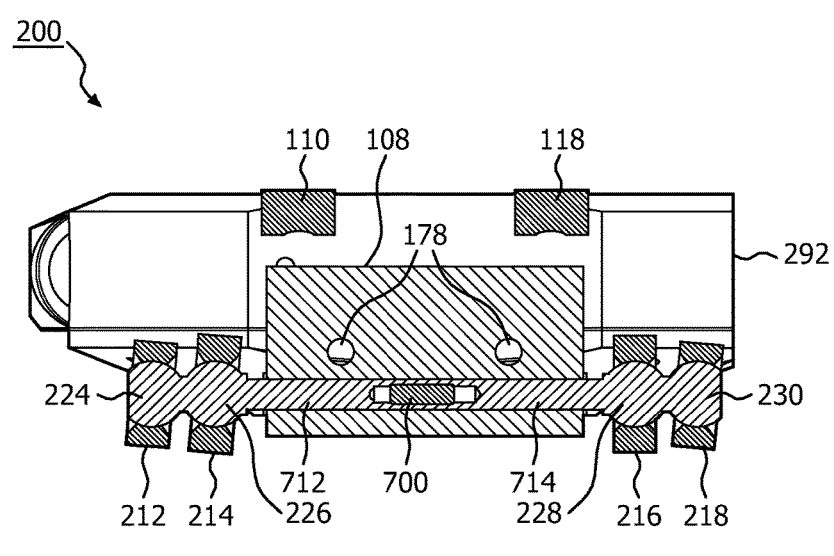
FIG. 7b shows a cross sectional view of the mechanism shown in FIGS. 2a through 2d along section line B.

FIG. 7b shows a cross sectional view of the mechanism 200 shown in FIGS. 2a through 2d along section line B. The cross section view passes through the first common axis shown in FIGS. 2a through 2d. FIG. 7b shows the construction details of the second ball joint, 224, third ball joint 226, fourth ball joint 228, and fifth ball joint 230. The second ball joint, 224 and third ball joint 226 are connected to a first axel 712. The third ball joint 226 and fourth ball joint 228 are connected to a second axel 714. The first axel 712 and the second axel are then connected using a threaded rod 700.

Figure 7C:
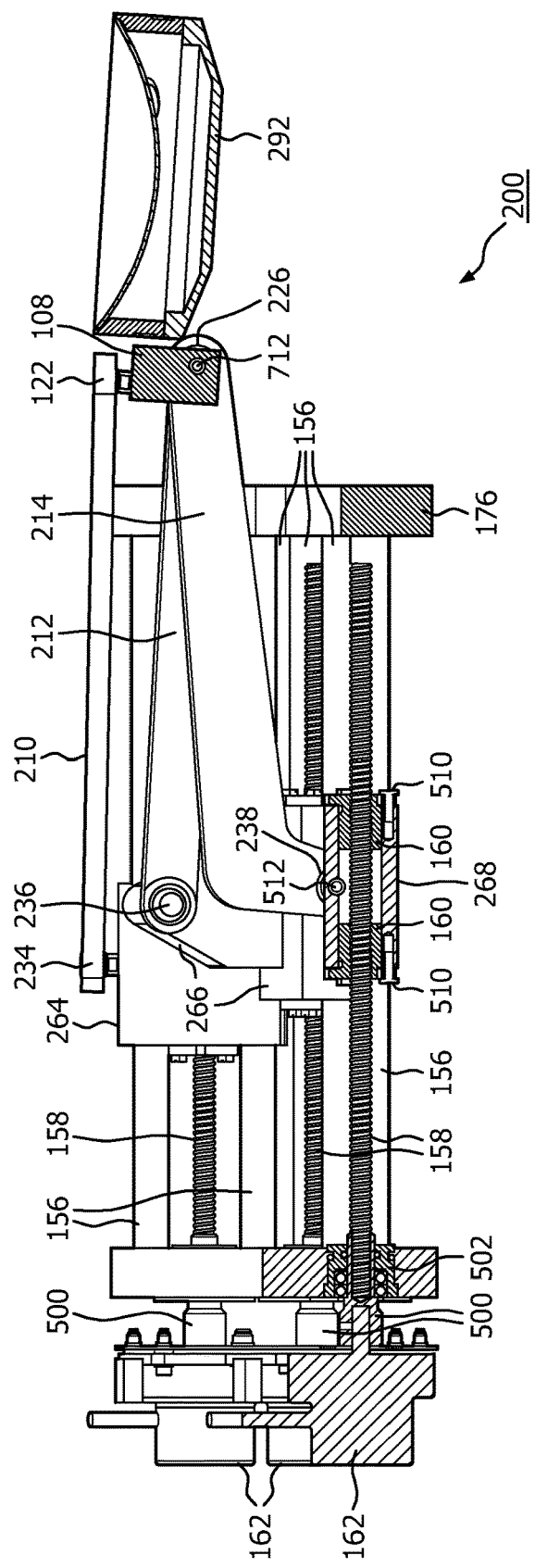
FIG. 7c shows a cross sectional view of the mechanism shown in FIGS. 2a through 2d along section line C.

FIG. 7c shows a cross sectional view of the mechanism 200 shown in FIGS. 2a through 2d along section line C. This figure shows the same cross sectional view shown in FIG. 5, except with additional elements of the mechanism 200 shown.

LIST OF REFERENCE NUMERALS

100 Mechanism
102 X axis
104 Y axis
106 Z axis
108 Positioning plate
110 First rod
112 Second rod
114 Third rod
116 Fourth rod
118 Fifth rod
120 Sixth rod
122 First ball joint
124 Second ball joint
126 Third ball joint
128 Fourth ball joint
130 Fifth ball joint
132 Sixth ball joint
134 Seventh ball joint
136 Eighth ball joint
138 Ninth ball joint
140 Tenth ball joint
142 Eleventh ball joint
144 Twelfth ball joint
146 First linear drive
148 Second linear drive
150 Third linear drive
156 Rod
158 screw drive rod
160 Threaded element
162 Ultrasonic motor
164 First drive block
166 Second drive block
168 Third drive block
174 Mechanism support
176 Plate
178 Threaded holes for mounting ultrasonic transducer
180 First common axis
182 Second common axis
184 Third common axis
186 Fourth common axis
188 Fifth common axis
190 Sixth common axis
200 Mechanism
202 Rotation about x axis
204 Rotation about y axis
208 Positioning plate
210 First rod
212 Second rod
214 Third rod
216 Fourth rod
218 Fifth rod
220 Sixth rod
222 First ball joint
224 Second ball joint
226 Third ball joint
228 Fourth ball joint
230 Fifth ball joint
232 Sixth ball joint
234 Seventh ball joint
236 Eighth ball joint
238 Ninth ball joint
240 Tenth ball joint
242 Eleventh ball joint
244 Twelfth ball joint
246 First linear drive
248 Second linear drive
250 Third linear drive
252 Fourth linear drive
254 Fifth linear drive
264 First drive block
266 Second drive block
268 Third drive block
270 Fourth drive block
272 Fifth drive block
280 First common axis
282 Second common axis
292 Ultrasonic transducer
300 Magnetic resonance imaging system
302 High intensity focused ultrasound system
304 transducer
306 Fluid filled region
308 Positioning block
310 Mechanism
312 Actuation system
314 Control system
316 Embedded system 317 Gap in subject support
318 Subject
319 Subject support
320 Transducer power supply
322 Magnet
324 Gradient power supply
326 Magnetic field gradient coil
328 coil
330 Radio frequency transceiver
332 Computer system
334 Hardware interface
336 User interface
338 Microprocessor
340 Memory
342 Storage
344 Computer program product
346 Magnetic resonance imaging control module
348 High intensity focused ultrasound control module
350 Image reconstruction module
352 Imaging data
354 Imaging zone
356 Path of ultrasound
358 Sonication zone
500 Coupler
502 Insert
504 Ball bearing
506 Static sealing element
508 Rotational sealing element
510 Screw
512 Axel
700 Threaded rod
712 First axel
714 Second axel
A Cross sectional line A
B Cross sectional line B
C Cross sectional line C

The invention claimed is:

1. A high intensity focused ultrasound positioning mechanism for positioning a high intensity focused ultrasound transducer, the mechanism comprising:
a positioning plate adapted for receiving the high intensity focused ultrasound transducer;
a mechanism support adapted for mounting the positioning mechanism;
a plurality of rods, wherein each rod has a first end and a second end, wherein the first end of each rod forms a separate ball joint with the positioning plate, wherein the plurality of rods are configured to move the positioning plate in at least three degrees of freedom; and
a plurality of linear drives, wherein the plurality of linear drives are mounted to the mechanism support, wherein each of the linear drives comprises a drive block, wherein the second end of each of the plurality of rods forms a separate ball joint with one of the drive blocks, wherein the positioning plate is movable along three orthogonal axes.

2. The mechanism of claim 1, wherein the plurality of rods comprises a first rod, a second rod, a third rod, a fourth rod, a fifth rod, and a sixth rod;
wherein the plurality of linear drives comprises a first linear drive, a second linear drive, and a third linear drive; wherein the first linear drive comprise a first drive block; wherein the second linear drive comprises a second drive block; and wherein the third linear drive comprises a third drive block;
wherein the first end of the first rod forms a first ball joint with the positioning plate;
wherein the first end of the second rod forms a second ball joint with the positioning plate;
wherein the first end of the third rod forms a third ball joint with the positioning plate;
wherein the first end of the fourth rod forms a fourth ball joint with the positioning plate;
wherein the first end of the fifth rod forms a fifth ball joint with the positioning plate;
wherein the first end of the sixth rod forms a sixth ball joint with the positioning plate;
wherein the second end of the first rod forms a seventh ball joint with the first drive block;
wherein the second end of the second rod forms an eighth ball joint with the first drive block;
wherein the second end of the third rod forms a ninth ball joint with the second drive block;
wherein the second end of the fourth rod forms a tenth ball joint with the second drive block;
wherein the second end of the fifth rod forms a eleventh ball joint with the third drive block; and
wherein the second end of the sixth rod forms a twelfth ball joint with the third drive block.

3. The mechanism of claim 2, wherein the first and second ball joints are mounted on a first common axis; wherein the second and third ball joints are mounted on a second common axis; wherein the fourth and fifth ball joints are mounted on a third common axis; wherein the seventh and eighth ball joints are mounted on a fourth common axis; wherein the ninth and tenth ball joints are mounted on a fifth common axis; and wherein the eleventh and twelfth ball joints are mounted on a sixth common axis.

4. The mechanism of claim 1, wherein at least one of the plurality of linear drives comprises a linear slide, a screw drive rod, and a bearing; and wherein at least one of the plurality of linear drives is actuated by an ultrasound motor.

5. The mechanism of claim 4, wherein the linear slide, the screw drive, and the bearing are ceramic.

6. The mechanism of claim 1, wherein at least one of the plurality of rods comprises plastic.

7. The mechanism of claim 1, wherein at least one of the plurality of rods comprise Acetal polyoxymethylene plastic.

8. The mechanism of claim 1, wherein at least one of the first through twelfth ball joints comprises a titanium ball.

9. A high intensity focused ultrasound unit, wherein the high intensity focused ultrasound unit comprises:
a mechanism according to any one of the preceding claims;
an actuation system for actuating the mechanism;
a control system for controlling the actuation system; and
a high intensity focused ultrasound transducer.

10. A magnetic resonance imaging system, the magnetic resonance imaging system comprising:
a high intensity focused ultrasound unit according to claim 9;
a magnet for generating a magnetic field for orientating the magnetic spins of nuclei;
a radio frequency system comprising a coil calibrated for acquiring magnetic resonance imaging data;
a magnetic field gradient coil for spatially encoding the orientation of the magnetic spins of nuclei; and
a computer system for constructing images from the magnetic resonance imaging data and for controlling the operation of the magnetic resonance imaging system, wherein the computer system is adapted for controlling the high intensity focused ultrasound unit.

11. A method of actuating a high intensity focused ultrasound positioning mechanism according to claim 1, the method comprising the steps of:
- calculating a trajectory of the mechanism from a first position to a second position;
- generating an actuation plan using the calculated trajectory; and
- actuating the mechanism from the first position to the second position using the actuation plan.

12. A non-transitory computer readable medium comprising a computer program product comprising machine executable-instructions for execution by a control system, wherein the control system is adapted for controlling the actuation of a high intensity focused ultrasound positioning mechanism according to claim 1, the computer program product comprising the steps of:
- calculating a trajectory of the mechanism from a first position to a second position;
- generating an actuation plan using the calculated trajectory; and
- actuating the mechanism from the first position to the second position using the actuation plan.

\* \* \* \* \*